US012648807B2

(12) United States Patent
Mangual-Soto et al.

(10) Patent No.: US 12,648,807 B2
(45) Date of Patent: Jun. 9, 2026

(54) SYSTEMS AND METHODS FOR ASSESSING ABLATION LESIONS

(71) Applicant: St. Jude Medical, Cardiology Division, Inc., St. Paul, MN (US)

(72) Inventors: Jan O. Mangual-Soto, Rho (IT); Louis-Philippe Richer, Montreal (CA); Chunlan Jiang, Crystal, MN (US); Cyrille Casset, Saint Selve (FR); Craig Markovitz, Leipzig (DE)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1024 days.

(21) Appl. No.: 17/309,229

(22) PCT Filed: Feb. 10, 2020

(86) PCT No.: PCT/US2020/017532
§ 371 (c)(1),
(2) Date: May 10, 2021

(87) PCT Pub. No.: WO2020/171998
PCT Pub. Date: Aug. 27, 2020

(65) Prior Publication Data
US 2021/0401492 A1      Dec. 30, 2021

Related U.S. Application Data

(60) Provisional application No. 62/808,462, filed on Feb. 21, 2019.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/6885* (2013.01); *A61B 18/1206* (2013.01);
(Continued)

(58) Field of Classification Search
CPC .................... A61B 18/1492; A61B 2018/0088
See application file for complete search history.

(56) References Cited

U.S. PATENT DOCUMENTS

2010/0113985 A1     5/2010   Thapliyal et al.
2010/0312095 A1*   12/2010   Jenkins .................. A61B 5/418
                                                        600/411
(Continued)

OTHER PUBLICATIONS

Kwiecinski et al, Quantitative evaluation of atrial radio frequency ablation using intracardiac shear-wave elastography, Med. Phys., 41:11 (2014). (Year: 2014).*

(Continued)

*Primary Examiner* — Linda C Dvorak
*Assistant Examiner* — Ryan T Clark
(74) *Attorney, Agent, or Firm* — Wiley Rein LLP

(57)                    ABSTRACT

Disclosed herein is a system for assessing ablation lesions. The system includes an ablation catheter configured to ablate a target cardiac tissue site to form an ablation lesion thereon, and a mechanical probe operable to impart mechanical force to the target cardiac tissue site. The mechanical probe includes at least one sensor configured to measure a mechanical response of the target cardiac tissue site to the mechanical force. The system further includes a controller communicatively coupled to the mechanical probe, and configured to determine systolic and diastolic stiffness values of the target cardiac tissue site based on the mechanical response. The controller is further configured to determine a transmurality value of the ablation lesion based on the determined systolic and diastolic stiffness values.

14 Claims, 6 Drawing Sheets

(51) Int. Cl.
  *A61B 18/12* (2006.01)
  *A61B 18/00* (2006.01)

(52) U.S. Cl.
  CPC .............. *A61B 2018/00577* (2013.01); *A61B 2018/00672* (2013.01); *A61B 2018/00678* (2013.01); *A61B 2018/0088* (2013.01)

(56) References Cited

U.S. PATENT DOCUMENTS

| | | | |
|---|---|---|---|
| 2011/0112400 A1* | 5/2011 | Emery | A61N 7/00 601/3 |
| 2016/0213282 A1 | 7/2016 | Leo et al. | |
| 2018/0271577 A1 | 9/2018 | Bharat et al. | |
| 2019/0125438 A1* | 5/2019 | Berman | A61B 18/1492 |

OTHER PUBLICATIONS

Kwiecinski Wojciech et al, "Quantitative Evaluation of Atrial Radio Frequency Ablation using Intracardiac Shear-Wave Elastography," Medical Physics, AIP, Oct. 20, 2014 (Oct. 20, 2014), p. 1-p. 10, vol. 41, No. 11, XP012191063, ISSN: 0094-2405, DOI: 10.1118/1. 4896820, Melville, NY, USA.
International Search Report and Written Opinion for PCT/US2020/ 017532, dated May 29, 2020, 13 pages.

* cited by examiner

SYSTEMS AND METHODS FOR ASSESSING ABLATION LESIONS

CROSS-REFERENCE TO RELATED APPLICATIONS

This application is a national stage entry of PCT/US2020/017532, filed Feb. 10, 2020, which claims priority to provisional application Ser. No. 62/808,462, filed Feb. 21, 2019, the disclosures of which are incorporated herein by reference in their entirety.

BACKGROUND OF THE DISCLOSURE a. Field of the Disclosure

The present disclosure relates generally to methods, systems, and apparatuses for performing an ablation procedure. More particularly, the present disclosure relates to ablation systems and methods for assessing the transmurality of ablation lesions.

b. Background

Heart arrhythmias are conditions causing an irregular heartbeat that can result in blood clots, stroke, heart failure, and other cardiac complications. It is believed that the primary cause of arrhythmias is stray electrical signals within the heart, such as within the left or right atrium. It is generally known that ablation therapy may be used to treat heart arrhythmias, including atrial fibrillation (AF), ventricular tachycardia (VT), and other conditions. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct heart arrhythmias. The ablation catheter imparts ablative energy (e.g., radiofrequency energy) to cardiac tissue to create a lesion in the cardiac tissue. This lesion disrupts undesirable electrical pathways and thereby limits or prevents stray electrical signals that lead to arrhythmias.

In ablation therapy, it is generally recognized that transmural lesions are effective at preventing stray electrical signals from being transmitted because transmural lesions penetrate the full thickness of the ablated tissue. It is also desirable in ablation therapy to limit the amount of collateral tissue damage during the formation of transmural lesions. However, conventional ablation treatments and techniques are less than optimal at measuring the transmurality of ablation lesions in clinical environments and settings, making it difficult to assess when to terminate the ablation procedure at a point when sufficient tissue has been destroyed to provide a clinically efficacious (transmural) ablation lesion. For example, ultrasound imaging techniques, used in research or laboratory settings, are not suitable for use in clinical environments because ultrasound imaging equipment is unsuitable for use within the cardiac chamber, and capturing reliable images of the ablated region (i.e., a relatively small, fixed point) is made difficult due to the cardiac chamber moving and blood flow.

Accordingly, a need exists for improved systems and methods for assessing the transmurality of ablation lesions.

SUMMARY OF THE DISCLOSURE

The present disclosure is directed to a system for assessing ablation lesions. The system includes an ablation catheter configured to ablate a target cardiac tissue site to form an ablation lesion thereon, and a mechanical probe operable to impart mechanical force to the target cardiac tissue site. The mechanical probe includes at least one sensor configured to measure a mechanical response of the target cardiac tissue site to the mechanical force. The system further includes a controller communicatively coupled to the mechanical probe, and configured to determine systolic and diastolic stiffness values of the target cardiac tissue site based on the mechanical response. The controller is further configured to determine a transmurality value of the ablation lesion based on the determined systolic and diastolic stiffness values.

The present disclosure is further directed to a method for assessing an ablation lesion formed at a target cardiac tissue site by an ablation catheter. The method includes imparting mechanical force to the target cardiac tissue site with a mechanical probe, and measuring a mechanical response of the target cardiac tissue site with at least one sensor of the mechanical probe. The method further includes determining, using a controller communicatively coupled to the mechanical probe, systolic and diastolic stiffness values of the target cardiac tissue site based on the mechanical response. The method further includes determining, using the controller, a transmurality value of the ablation lesion based on the determined systolic and diastolic stiffness values.

The present disclosure is further directed to a lesion assessment system for assessing an ablation lesion formed at a target cardiac tissue site. The system includes a mechanical probe operable to impart mechanical force to the target cardiac tissue site. The mechanical probe includes at least one sensor configured to measure a mechanical response of the target cardiac tissue site to the mechanical force. The system further includes a controller communicatively coupled to the mechanical probe, and configured to determine systolic and diastolic stiffness values of the target cardiac tissue site based on the mechanical response. The controller is further configured to determine a transmurality value of the ablation lesion based on the determined systolic and diastolic stiffness values.

DETAILED DESCRIPTION OF THE DISCLOSURE

The present disclosure is directed to systems and methods for assessing ablation lesions and, more particularly, to assessing the transmurality or depth of ablation lesions formed in cardiac tissue. Embodiments of the lesion assessment systems and methods disclosed herein facilitate evaluating ablation lesions in real-time or substantially in real-time, during intra-operative scenarios. The various approaches described herein may therefore allow an operator of an ablation system to receive immediate or substantially immediate feedback regarding the transmurality or depth of an ablation lesion. Based on this feedback, the operator can determine whether to cease an ablation procedure, or to perform the ablation procedure for additional time to facilitate formation of a transmural lesion. Embodiments of the lesion assessment systems and methods thereby facilitate reducing arrhythmia recurrence, and preventing additional electrophysiology procedures for patients.

In particular, embodiments of the present disclosure utilize known relationships between mechanical properties (e.g., tissue stiffness) of healthy cardiac tissue and ablated cardiac tissue to assess the transmurality of an ablation lesion. More specifically, embodiments of the present disclosure use a mechanical probe to measure or determine one or more mechanical properties of cardiac tissue, such as tissue stiffness, at a target cardiac tissue site where an ablation lesion is formed or is to be formed. Based on the measured mechanical properties, the systems and methods disclosed herein determine a transmurality value of the ablation lesion formed at the target cardiac tissue site indicative of whether the ablation lesion is transmural or not. Unlike some previous lesion assessment systems, the lesion assessment systems and methods of the present disclosure can be employed in clinical setups (i.e., in real-time intra-operative scenarios), and thereby enable real-time or substantially real-time feedback on ablation lesions formed during ablation procedures.

Figure 1:
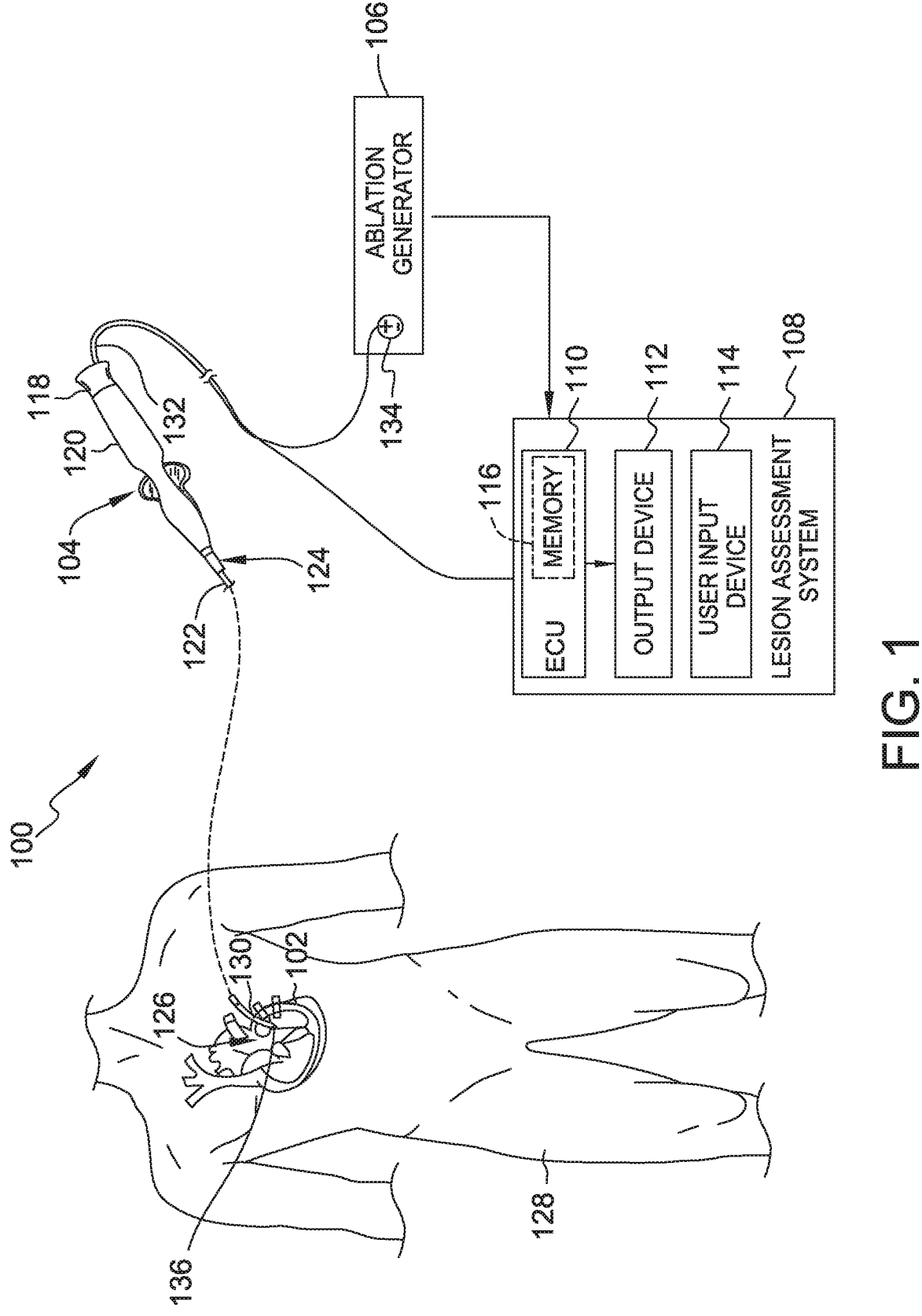
FIG. 1 is a schematic and block diagram view of an ablation system that includes an ablation lesion assessment system.

Referring now to the drawings, FIG. 1 illustrates one exemplary embodiment of an ablation system 100 for performing one or more diagnostic and/or therapeutic functions that include components for presenting information representative of lesion formations in cardiac tissue 102 during and/or after an ablation procedure performed thereon. It should be understood, however, that the system 100 has equal applicability to ablation procedures on other tissues as well, and is not limited to ablation procedures on cardiac tissue.

The system 100 includes a medical device (such as, for example, a catheter 104), an ablation generator 106, and a lesion assessment system 108 for assessing properties (e.g., transmurality) of one or more lesions formed in cardiac tissue 102 during an ablation procedure. The lesion assessment system 108 may include, for example and without limitation, a controller or electronic control unit (ECU) 110, an output device 112, user input device 114, and memory 116. Alternatively, controller 110 and/or output device 112 may be separate and distinct from, but electrically connected to and configured for communication with, the lesion assessment system 108. In some embodiments, the lesion assessment system 108 may be implemented in combination with, as part of, or incorporated within other systems and/or sub-systems of the ablation system 100 including, for example and without limitation, imaging systems, mapping systems, navigation systems, and any other system or sub-system of the ablation system 100.

The catheter 104 is provided for examination, diagnosis, and/or treatment of internal body tissues, such as cardiac tissue 102. In an exemplary embodiment, the catheter 104 comprises a radio frequency (RF) ablation catheter. It should be understood, however, that the catheter 104 is not limited to an RF ablation catheter. Rather, in other embodiments, the catheter 104 may comprise an irrigated catheter and/or other types of ablation catheters (e.g., cryoablation, ultrasound, irreversible electroporation, balloon, basket, single electrode, bullet, etc.).

In an exemplary embodiment, the catheter 104 is electrically connected to the ablation generator 106 to allow for the delivery of RF energy. The catheter 104 may include a cable connector or interface 118, a handle 120, a shaft 122 having a proximal end 124 and distal end 126 (as used herein, "proximal" refers to a direction toward the end of catheter 104 near the operator, and "distal" refers to a direction away from the operator and (generally) inside the body of a subject or patient 128), and one or more electrodes 130 mounted in or on shaft 122 of catheter 104. In an exemplary embodiment, electrode 130 is disposed at or near distal end 126 of shaft 122, with electrode 130 comprising an ablation electrode disposed at the extreme distal end 126 of shaft 122 for contact with cardiac tissue 102. Catheter 104 may further include other conventional components such as, for example and without limitation, sensors, additional electrodes (e.g., ring electrodes) and corresponding conductors or leads, thermocouples, or additional ablation elements, e.g., a high intensity focused ultrasound ablation element and the like.

Connector 118 provides mechanical and electrical connection(s) for cables 132 extending from the ablation generator 106, lesion assessment system 108, and other systems and/or sub-systems of the ablation system 100. Connector 118 is conventional in the art and is disposed at the proximal end of catheter 104.

Handle 120 provides a location for the operator to hold catheter 104 and may further provide means for steering or guiding shaft 122 within the patient 128. For example, handle 120 may include means to change the length of a guidewire extending through catheter 104 to distal end 126 of shaft 122 to steer shaft 122. Handle 120 is also conventional in the art and it will be understood that the construction of handle 120 may vary. In another exemplary embodiment, catheter 104 may be robotically driven or controlled. Accordingly, rather than an operator manipulating a handle to steer or guide catheter 104, and shaft 122 thereof, in particular, a robot is used to manipulate catheter 104.

Shaft 122 is generally an elongated, tubular, flexible member configured for movement within the patient 128. Shaft 122 supports, for example and without limitation, electrode 130, associated conductors, and possibly additional electronics used for signal processing or conditioning. Shaft 122 may also permit transport, delivery and/or removal of fluids (including irrigation fluids, cryogenic ablation fluids, and bodily fluids), medicines, and/or surgical tools or instruments. Shaft 122 may be made from conventional materials such as polyurethane, and defines one or more lumens configured to house and/or transport at least electrical conductors, fluids, or surgical tools. Shaft 122 may be introduced into cardiac tissue 102 through a conventional introducer. Shaft 122 may then be steered or guided within cardiac tissue 102 to a desired location with guidewires or other means known in the art.

Ablation generator 106 generates, delivers, and controls RF energy output by ablation catheter 104 and electrode 130 thereof, in particular. In an exemplary embodiment, ablation generator 106 includes RF ablation signal source 134 configured to generate an ablation signal that is output across a pair of source connectors: a positive polarity connector SOURCE (+), which may be electrically connected to tip electrode 130 of catheter 104; and a negative polarity connector SOURCE (−). It should be understood that the term connectors as used herein does not imply a particular type of physical interface mechanism, but is rather broadly contemplated to represent one or more electrical nodes. Source 134 is configured to generate a signal at a predetermined frequency in accordance with one or more user specified parameters (e.g., power, time, etc.) and under the control of various feedback sensing and control circuitry as is known in the art. Source 134 may generate a signal, for example, with a frequency of about 450 kHz or greater. Ablation system 100 may also monitor various parameters associated with the ablation procedure including, for example, impedance, the temperature at the distal tip of the catheter, applied ablation energy, and the position of the catheter, and provide feedback to the operator or another component within system 100 regarding these parameters.

In accordance with the present disclosure, the ablation system 100 described above may additionally include a mechanical probe 136 for assessing the transmurality or depth of ablation lesions formed in cardiac tissue 102 with the ablation system 100. In some embodiments, for example, the mechanical probe 136 measures or detects one or more mechanical properties of the cardiac tissue 102 (e.g., tissue stiffness) at and/or adjacent to a lesion, and the lesion assessment system 108 (e.g., the controller 110) determines or estimates the transmurality or depth of the lesion based on the one or more mechanical properties. In particular, the mechanical probe 136 is operable to impart mechanical force to the cardiac tissue 102 at and/or adjacent to a lesion formed therein, and measure a mechanical response of the cardiac tissue 102. The mechanical response data is output to the lesion assessment system 108, which processes the data to determine one or more mechanical properties of the cardiac tissue 102. Based on the determined mechanical properties of the cardiac tissue 102, the lesion assessment system 108 (e.g., the controller 110) is further configured to determine the transmurality of the ablation lesion formed on the cardiac tissue 102, and output (e.g., via output device 112) a suitable message, notification, and/or alert to an operator of the ablation system 100. Based on the output, the operator may terminate the ablation procedure at the lesion site (e.g., when it is determined that the lesion is a transmural lesion), or perform the ablation procedure at the lesion site for additional time (e.g., when it is determined that the lesion is not transmural).

Figure 2:
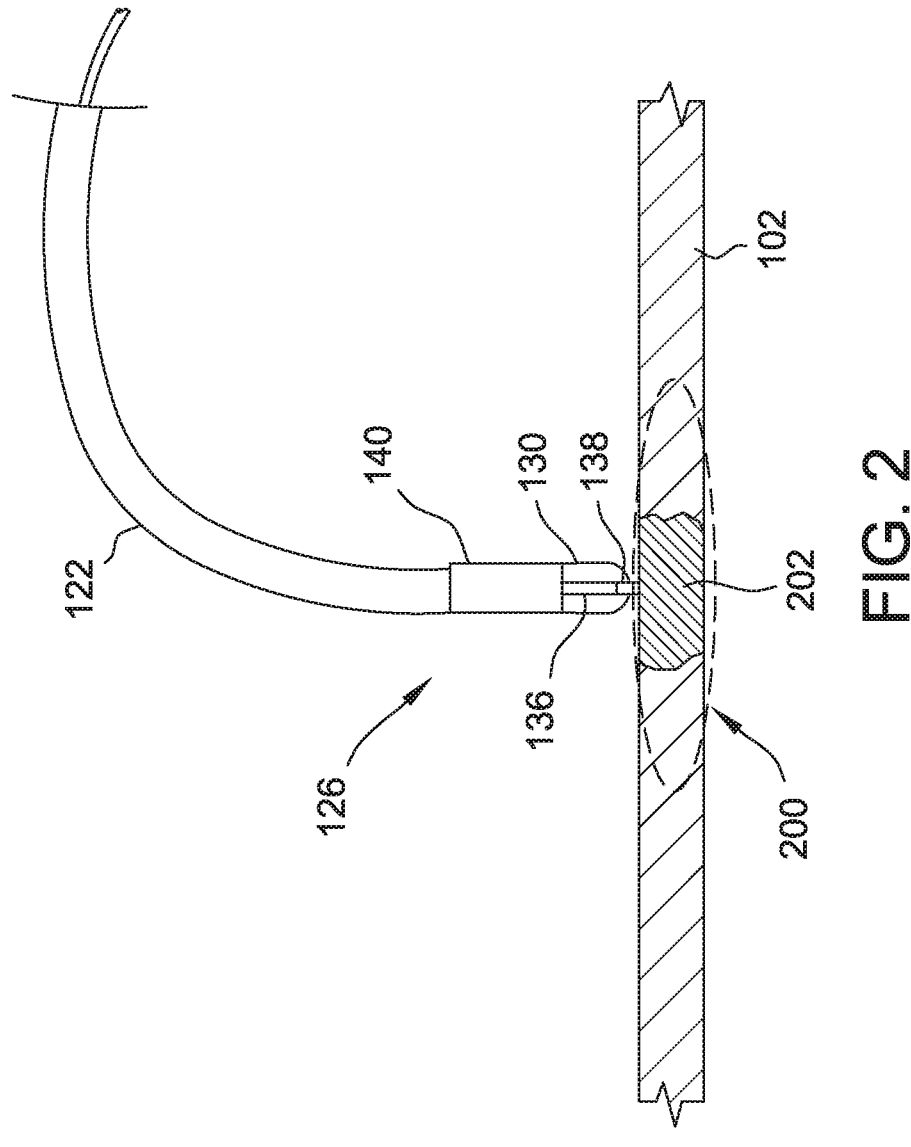
FIG. 2 is a schematic view of a distal tip of an ablation catheter included in the ablation system shown in FIG. 1.

FIG. 2 is a schematic view of the distal tip 126 of the catheter shaft 122, showing the mechanical probe 136 adjacent a target cardiac tissue site 200 at which an ablation lesion 202 is formed. A "target cardiac tissue site" refers to a site in cardiac tissue 102 at which an ablation lesion 202 is formed, or at which an ablation lesion 202 is intended to be formed. As shown in FIG. 2, the target cardiac tissue site 200 may include both ablated cardiac tissue and healthy (i.e., unablated) cardiac tissue.

In the illustrated embodiment, the mechanical probe 136 is incorporated as a component of the ablation catheter 104 (specifically, at the distal end 126 of the ablation catheter 104), although it should be understood that the mechanical probe 136 may be implemented as part of another catheter (e.g., a mapping or imaging catheter) or as a dedicated, stand-alone catheter (i.e., separate from other catheters). The mechanical probe 136 may include one or more suitable devices for imparting mechanical force to the cardiac tissue 102 including, for example and without limitation, a mechanical oscillator (e.g., transducers, vibrators, etc.), a shaft, a pin, a piston, and any other suitable device or devices capable of imparting a mechanical force to cardiac tissue 102. Further, as shown in FIG. 2, the mechanical probe 136 includes one or more sensors 138 configured to measure a mechanical response of the cardiac tissue 102 to the applied force from the mechanical probe 136. Suitable sensors for detecting the mechanical response of the cardiac tissue 102 include, for example and without limitation, pressure sensors (e.g., transducers), optical sensors, displacement sensors, electro-magnetic sensors, magnetic sensors, acoustic sensors, and any other suitable sensor or sensors that enable the ablation system 100 to function as described herein. In some embodiments, the mechanical probe 136 also includes a contact force sensor 140 that measures or detects an amount of applied force between the mechanical probe 136 and the cardiac tissue 102. The measured contact force may be used, for example and without limitation, to ensure consistency across mechanical response measurements, to trigger an output of mechanical force by the mechanical probe 136 (e.g., upon a pre-determined contact force being applied to the cardiac tissue 102), and to measure one or more mechanical properties of the cardiac tissue 102. The mechanical response data collected by the mechanical probe 136 is output to the controller 110 for determining a transmurality value of the lesion, as described in further detail herein.

The mechanical probe 136, including the sensor 138, may be configured to measure one or more mechanical responses of the cardiac tissue to facilitate determination of the transmurality value. Suitable mechanical responses that the mechanical probe 136 can measure include, for example and without limitation, a transmission speed of mechanical or oscillatory waves through the cardiac tissue, attenuation or deformation of mechanical or oscillatory waves in the cardiac tissue, elasticity of the cardiac tissue, strain or displacement of the cardiac tissue under a known force, and any other measurable mechanical response of cardiac tissue that enables the ablation system 100 to function as described herein.

Embodiments of the present disclosure utilize known relationships between the stiffness of healthy cardiac tissue and ablated cardiac tissue to assess the transmurality of an ablation lesion. More specifically, the stiffness of ablated cardiac tissue is greater than healthy (i.e., un-ablated) cardiac tissue, typically by a factor of 2-3 or more depending on the type of cardiac tissue. Additionally, healthy (i.e., un-ablated) cardiac tissue is approximately 8-10 times stiffer in systole than in diastole. Thus, the transmurality or depth of an ablation lesion may be assessed by analyzing the stiffness of cardiac tissue and, more particularly, by analyzing systolic and diastolic tissue stiffness in healthy (unablated) cardiac tissue and ablated cardiac tissue. Embodiments of the present disclosure utilize mechanical response data collected by the mechanical probe 136 to determine a transmurality value of ablation lesions based on tissue stiffness at a target cardiac tissue site 200.

In some embodiments, mechanical response data is collected by the mechanical probe 136 at the target cardiac tissue site 200 in both the systolic phase and the diastolic phase of the cardiac cycle. The mechanical response data is output to the controller 110, which determines systolic and diastolic stiffness values of the target cardiac tissue site 200 based on the mechanical response data. The systolic and diastolic stiffness values are values indicative of the stiffness of the cardiac tissue, and may be absolute values or relative values. The controller 110 is configured to determine a transmurality value of the ablation lesion 202 based on the determined stiffness values. The transmurality value is a value (e.g., a unitless number, such as a ratio) that is indicative of whether the ablation lesion is transmural. The transmurality value can be, for example and without limitation, a binary value (e.g., one of two values, one of which indicates a non-transmural lesion, the other of which indicates a transmural lesion), a percentage, a ratio, or any other suitable value capable of indicating a likelihood or probability that an ablation lesion is transmural. In some embodiments, for example, the controller 110 determines the transmurality value by determining a ratio of the systolic and diastolic stiffness values. A lower stiffness ratio (e.g., a ratio closer to one) is indicative of ablated tissue, and thus that the ablation lesion 202 is more likely to be transmural. A higher ratio (e.g., a ratio closer to 8-10) is indicative of healthy cardiac tissue, and thus that the ablation lesion is likely not transmural or that no lesion has been formed.

Additionally or alternatively, the controller 110 determines the transmurality value by determining a difference or change in the systolic/diastolic stiffness value ratio resulting from an ablation procedure. That is, the controller 110 determines the transmurality value by determining a change in the systolic/diastolic stiffness value ratio between healthy cardiac tissue and ablated cardiac tissue. In some embodiments, for example, control stiffness values (i.e., stiffness values of unablated cardiac tissue) are determined for the cardiac tissue at the target cardiac tissue site 200 based on a mechanical response of the healthy cardiac tissue at the target cardiac tissue site 200. For example, the mechanical response of healthy cardiac tissue at the target cardiac tissue site 200 can be measured in both systole and diastole prior to the ablation procedure. Additionally or alternatively, the mechanical response of healthy cardiac tissue can be measured at the target cardiac tissue site 200 by measuring the mechanical response of healthy cardiac tissue adjacent to the ablation lesion 202. The mechanical response data of the healthy cardiac tissue is output to the controller 110, which determines control systolic and diastolic stiffness values based on the mechanical response. In some embodiments, the controller 110 determines the transmurality value by determining the difference or change between the systolic/diastolic stiffness value ratio for ablated tissue and the control systolic/diastolic stiffness value ratio. A large change in the systolic/diastolic stiffness value ratio (e.g., a change of 4 or greater) indicates that the ablation lesion 202 is more likely transmural, whereas a smaller change in the systolic/diastolic stiffness value ratio (e.g., a change of 3 or less) indicates that the ablation lesion 202 is less likely to be transmural.

In implementations where the mechanical probe 136 includes a contact force sensor 140, systolic and diastolic stiffness values may be determined based on a mechanical response of the cardiac tissue measured at the same, pre-determined contact force. For example, in some embodiments, the mechanical response of healthy cardiac tissue at the target cardiac tissue site 200 may be measured and recorded while a pre-determined contact force, measured by the contact force sensor 140, is applied to the cardiac tissue with the mechanical probe 136. The mechanical response may be measured in both the systolic and diastolic phases of the cardiac cycle while applying the same, pre-determined contact force with the mechanical probe 136. Additionally, the mechanical response of ablated cardiac tissue at the target cardiac tissue site 200 may likewise be measured and recorded while the same pre-determined contact force is applied to the cardiac tissue in both the systolic and diastolic phases. Recording the mechanical response of cardiac tissue while the same contact force is applied to the cardiac tissue facilitates consistent measurements and determining more accurate stiffness values. Because the contact force between the mechanical probe 136 and the target cardiac tissue site 200 will vary at different cardiac phases for a given applied external pressure (e.g., applied by the operator), the external pressure applied by the mechanical probe 136 may be varied or adjusted to achieve the same contact force in systole and diastole. For example, a greater external pressure may need to be applied to the mechanical probe 136 to achieve a 20 gram (g) contact force in diastole because cardiac tissue is generally less stiff in diastole. On the other hand, a smaller external pressure may need to be applied to mechanical probe 136 to achieve a 20 g contact force in systole because cardiac tissue is generally stiffer in systole. Stated another way, the average contact force applied by the mechanical probe 136 will be higher to achieve a given contact force in diastole than the average contact force needed to achieve the same contact force in systole.

To facilitate measuring contact force, measuring the mechanical response of cardiac tissue, or otherwise assessing ablation lesions, the mechanical probe 136 may include technology similar to or the same as that used in the TactiCath™ contact force ablation catheter, commercially available from Abbott Laboratories. Additionally, or alternatively, the mechanical probe 136 and lesion assessment system 108 may include force sensing sensors, systems, and techniques illustrated and/or described in one or more of U.S. Pat. Nos. 8,048,063; 8,075,498; 8,182,433; 8,435,232; 8,567,265; 8,641,705; 8,932,288; 8,961,436; 9,237,920; 9,597,036; 9,907,618; 9,950,141, each of which is hereby incorporated by reference in its entirety as though fully set forth herein.

The controller 110 is configured to output the determined transmurality value to an operator of the ablation system 100 via the output device 112. In some embodiments, for example, the controller 110 presents the determined transmurality value to an operator of the ablation system 100 by displaying the determined transmurality value on a display device of the output device 112. Based on the determined transmurality value, the operator may perform the ablation procedure at the target cardiac tissue site 200 for additional time (e.g., when the determined transmurality value is indicative of a non-transmural lesion), or terminate the ablation procedure at the target cardiac tissue site 200 (e.g., when the determined transmurality value is indicative of a transmural lesion).

Additionally or alternatively, the controller 110 may be configured to generate at least one of an audibly-perceptible alert and a visually-perceptible alert when the determined transmurality value is above an upper threshold value and/or when the determined transmurality value is below a lower threshold value. For example, the controller 110 may be configured to compare the determined transmurality value to an upper threshold value and/or a lower threshold value, and generate, via the output device 112, at least one of the audibly-perceptible alert and visually-perceptible alert when the determined transmurality value is above the upper threshold value or below the lower threshold value. The alert may indicate to the operator that the determined transmurality value is indicative of a non-transmural lesion, and that the ablation procedure should be carried out for additional time. Alternatively, the alert may by an affirmative alert indicating that the determined transmurality value is indicative of a transmural lesion. For example, where the transmurality value is determined based on a ratio of the systolic and diastolic stiffness values, an upper threshold value (e.g., 5) may be used to generate an alert that indicates the lesion is likely not transmural. Additionally or alternatively, a lower threshold value (e.g., 3) may be used to generate an alert that indicates the lesion is likely transmural. In other embodiments, the upper and lower threshold values may be set at any suitable value that enables the ablation system 100 to function as described herein. Further, alerts may be generated in any suitable manner (e.g., affirmative and negative alerts) that enables the ablation system 100 to function as described herein.

Figure 3:
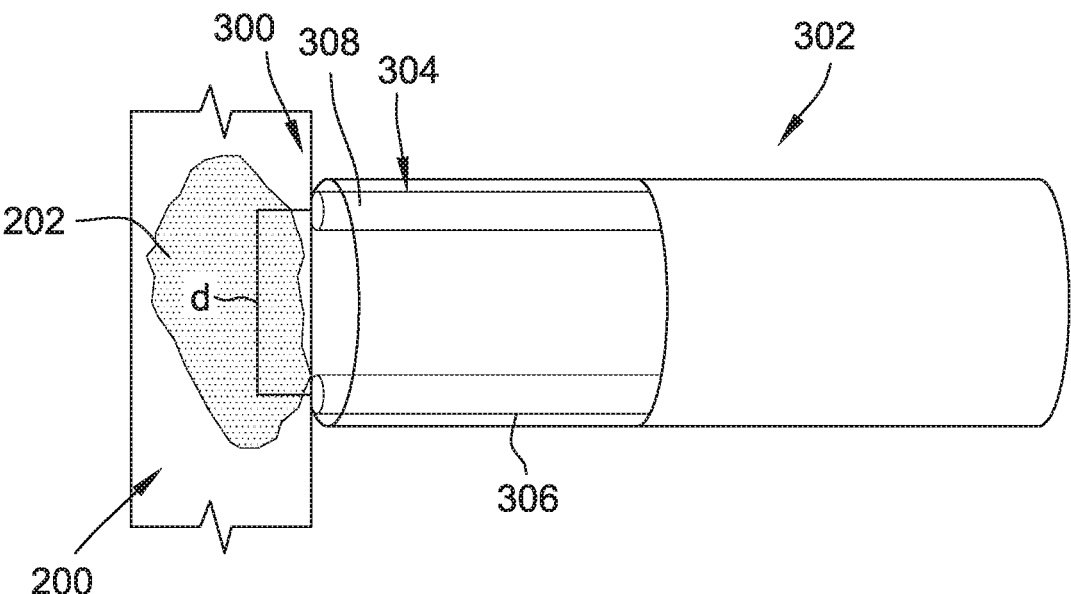
FIG. 3 is a schematic view of one exemplary embodiment of a mechanical probe suitable for use with the ablation system of FIG. 1.

FIG. 3 is a schematic view of one exemplary embodiment of a mechanical probe 300 suitable for use with the ablation system 100 of FIG. 1. In the illustrated embodiment, the mechanical probe 300 is shown adjacent to a target cardiac tissue site 200 at which an ablation lesion 202 has been formed. In this embodiment, the mechanical probe 300 is implemented as a stand-alone or dedicated catheter 302, although it should be understood that in other embodiments, the mechanical probe 300 may be implemented as part of or in combination with other catheters (e.g., ablation catheters, mapping catheters, imaging catheters, etc.). As shown in FIG. 3, the mechanical probe 300 includes a mechanical oscillator 304 configured to impart a mechanical wave or waves to the target cardiac tissue site 200, and a sensor 306 positioned at a known distance d from the mechanical oscillator 304 and configured to detect the mechanical wave as it propagates through the tissue. The mechanical probe 300 is communicatively coupled to the lesion assessment system 108 for outputting data and measurements (e.g., mechanical response measurements) thereto, and/or for receiving control signals therefrom.

In this embodiment, the mechanical probe 300 is designed to leverage the propensity of cardiac tissue to transmit a mechanical wave from one point to another as an indication of the tissue stiffness. That is, the mechanical response measured by the mechanical probe 300 in this embodiment is the transmission speed of mechanical or oscillatory waves through the cardiac tissue. More specifically, the mechanical probe 300 is configured to impart a mechanical wave or waves to the target cardiac tissue site 200 via the mechanical oscillator 304, and to detect the amount of time the mechanical wave takes to travel through the tissue using the sensor 306. The mechanical probe 300 is connected to the lesion assessment system 108 (shown in FIG. 1), and the controller 110 (shown in FIG. 1) is configured to determine the tissue stiffness value of the target cardiac tissue site 200 based on an amount of time for the mechanical wave generated by the mechanical oscillator 304 to travel the known distance d through the cardiac tissue from the mechanical oscillator 304 to the sensor 306. That is, the controller 110 is configured to determine the tissue stiffness value of the target cardiac tissue site 200 based on an amount of time associated with the mechanical wave traveling through the cardiac tissue from the mechanical oscillator 304 to the sensor 306.

The mechanical oscillator 304 may include any suitable device for imparting a mechanical wave or waves to the target cardiac tissue site 200. In the illustrated embodiment, the mechanical oscillator 304 includes a pin 308 operatively coupled to a vibrator (not shown) having a selectively variable frequency and amplitude output. In suitable embodiments, the mechanical oscillator 304 is configured to output a mechanical wave at a sub-ultrasonic frequency, such as in the range of 1 Hertz (Hz) to 1,000 Hz and, more suitably, in the range of 10 Hz to 100 Hz. In other embodiments, the mechanical oscillator 304 is configured to output a mechanical wave at any suitable frequency that enables the ablation system 100 to function as described herein.

The sensor 306 may likewise include any suitable sensor for detecting the mechanical wave as it propagates through the tissue. Suitable sensors include, for example and without limitation, a pin 306 operatively coupled to a transducer (not shown), and an optical sensor.

Figure 4:
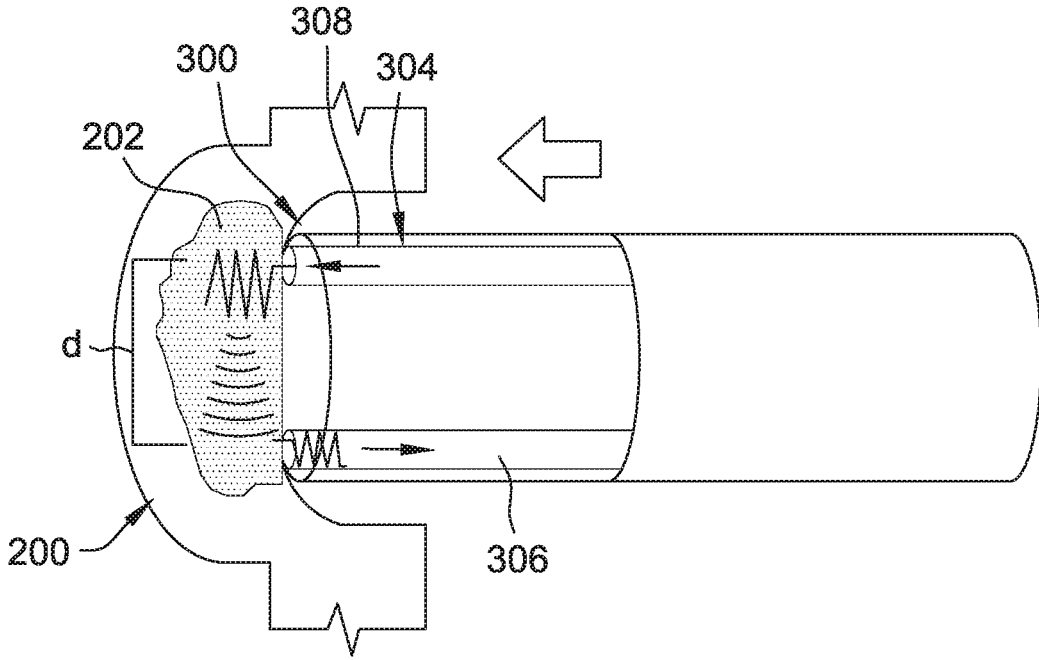
FIG. 4 is another schematic view of the mechanical probe shown in FIG. 3, illustrating an exemplary method of using the mechanical probe to measure tissue stiffness.

FIG. 4 illustrates an exemplary method of using the mechanical probe 300 of FIG. 3 to measure tissue stiffness. As shown in FIG. 4, in the exemplary method, the catheter 104 initially makes contact with the target cardiac tissue site 200 at a pre-determined contact force value. The pre-determined contact force value may be measured, for example, using a suitable contact force sensor, such as the contact force sensor 140 shown in FIG. 2. When reaching the pre-determined contact force values in systole and diastole, the mechanical probe 300 transmits one or more vibratory waves to the target cardiac tissue site 200 through the mechanical oscillator 304. In some embodiments, the controller 110 of the lesion assessment system 108 is configured to automatically transmit or output the mechanical wave in response to the contact force sensor detecting the pre-determined amount of contact force between the mechanical probe 300 and the target cardiac tissue site 200. The vibration frequency output by the mechanical oscillator may be fixed or variable. As shown in FIG. 4, the mechanical wave propagates through the cardiac tissue at the target cardiac tissue site 200, and eventually reaches the sensor 306 at the known distance d from the mechanical oscillator 304. The amount of time required for the wave to reach the sensor 306 is recorded by the controller 110, and used to determine systolic and diastolic tissue stiffness values of the target cardiac tissue site 200.

In some embodiments, the controller 110 may also record the vibration intensity and wave pattern detected by the sensor 306, and use these values, in addition to or alternatively to the amount of time required for the mechanical wave to reach the sensor 306, to determine systolic and diastolic tissue stiffness values of the target cardiac tissue site 200. In some embodiments, for example, the controller 110 may determine the systolic and diastolic tissue stiffness values based on a level of attenuation or deformation of the wave pattern detected by the sensor 306. For example, if the mechanical wave is highly attenuated or deformed, the controller 110 may determine that the lesion is not likely transmural because the high deformation or attenuation is indicative of less stiff tissue, and thus a non-transmural lesion. On the other hand, if the mechanical wave is only slightly attenuated or deformed, the controller 110 may determine that the lesion is likely transmural because little to no deformation or attenuation is indicative of stiffer tissue, and thus a transmural lesion. In other embodiments, the controller 110 may determine the systolic and diastolic tissue stiffness values based on a number of identified deflections in the mechanical wave pattern imparted to the target cardiac tissue site 200. For example, if the controller 110 detects a large number of deflections in the wave pattern, the controller 110 may determine that the lesion is not likely transmural because the large number of deflections is indicative of less stiff tissue, and thus a non-transmural lesion. On the other hand, if the controller 110 detects few or no deflections in the wave pattern, the controller 110 may determine that the lesion is likely transmural because fewer deflections in the wave pattern is indicative of stiffer tissue, and thus a transmural lesion. The systolic and diastolic tissue stiffness values of the target cardiac tissue site 200 are in turn used by the controller 110 to determine a transmurality value of the ablation lesion 202 in accordance with the techniques and methods described herein.

In some embodiments, the mechanical probe 300 and the lesion assessment system 108 are configured to isolate the vibration signal recorded by the sensor 306 from background "noise" or vibrations. In suitable embodiments, for example, the controller 110 is configured to record a control vibration signal based on measurements taken by the sensor 306 while the mechanical oscillator 304 is inactive, and determine an isolated vibration signal by subtracting or "factoring out" the control vibration signal from the vibration signal recorded by the sensor 306 while the mechanical oscillator 304 is active. These recordings may be timed with the systolic and diastolic cardiac phases to allow determination of tissue stiffness values for the two phases.

Figure 5:
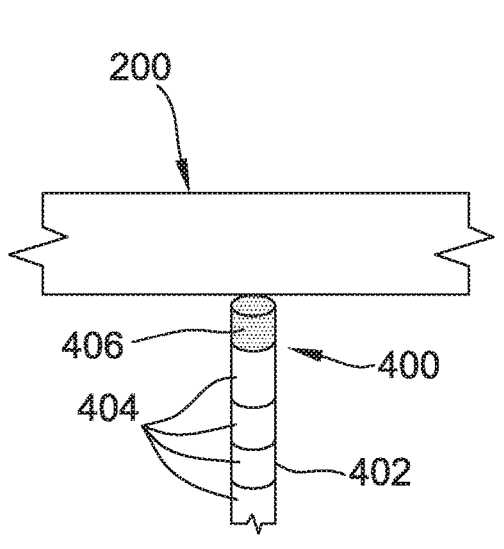
FIG. 5 is a schematic view of another exemplary embodiment of a mechanical probe suitable for use with the ablation system of FIG. 1.

FIG. 5 is a schematic view of another exemplary embodiment of a mechanical probe 400 suitable for use with the ablation system 100 of FIG. 1. In the illustrated embodiment, the mechanical probe 400 is shown adjacent to a target cardiac tissue site 200 prior to an ablation lesion 202 (shown in FIGS. 7 and 8) being formed. In this embodiment, the mechanical probe 400 is implemented as a stand-alone or dedicated catheter 402, although it should be understood that in other embodiments, the mechanical probe 400 may be implemented as part of or in combination with other catheters (e.g., ablation catheters, mapping catheters, imaging catheters, etc.). As shown in FIG. 5, the mechanical probe 400 includes a plurality of position sensors 404 configured to detect a position of the mechanical probe 400 in three-dimensional space. The illustrated embodiment includes four position sensors 404, although it should be understood that the mechanical probe 400 may include any suitable number of position sensors that enables the mechanical probe 400 to function as described herein, including fewer than or greater than four position sensors 404. Additionally, in this embodiment, the mechanical probe 400 includes a contact force sensor 406 that measures or detects an amount of applied force between the mechanical probe 400 and the target cardiac tissue site 200. In some embodiments, the contact force sensor 406 is the same as or has substantially the same configuration as the contact force sensor 140. The mechanical probe 400 is communicatively coupled to the lesion assessment system 108 for outputting data and measurements (e.g., mechanical response measurements) thereto, and/or for receiving control signals therefrom.

In this embodiment, the mechanical probe 400 is designed to measure cardiac tissue stiffness based on a measured amount of displacement resulting from an applied force. More specifically, the plurality of position sensors 404 are configured to measure a displacement amount of the target cardiac tissue site 200 resulting from a pre-determined contact force applied to the target cardiac tissue site 200 by the mechanical probe 400.

The position sensors 404 may include any suitable sensors for detecting the position of the mechanical probe 400 in three-dimensional space. Suitable sensors include, for example and without limitation, electro-magnetic sensors, magnetic sensors, acoustic sensors, and any other suitable sensor that enables detection of the mechanical probe 400 in space. In an exemplary embodiment, the plurality of sensors 404 includes electrodes that interact with an electric and/or magnetic field to enable detection of the position of the mechanical probe 400 in three-dimensional space. Additionally or alternatively, the mechanical probe 400 and lesion assessment system 108 may include technology similar to or the same as that used in the EnSite™ Velocity™ or EnSite Precision™ cardiac mapping and visualization system, commercially available from Abbott Laboratories. Additionally, or alternatively, the mechanical probe 400 and lesion assessment system 108 may include position sensors, localization and mapping systems, and techniques illustrated and/or described in one or more of U.S. Pat. Nos. 6,233,476; 6,556,695; 7,365,745; 7,774,051; 7,825,925; 7,855,707; 7,894,871; 7,988,639; 8,038,625; 8,130,221; 8,229,545; 8,253,725; 8,352,019; 8,364,253; 8,454,538; 8,454,589; 8,620,978; 8,647,284; 8,825,144; 8,805,490; 8,849,393; 9,026,196; 9,078,591; 9,111,175; 9,113,807; 9,137,611; 9,159,162; 9,198,601; 9,204,927; 9,237,920; 9,392,973; 9,339,325; 9,486,152; 9,549,689; 9,560,988; 9,585,586; 9,591,990; 9,597,036; 9,610,027; 9,956,049, each of which is hereby incorporated by reference in its entirety as though fully set forth herein.

Figure 6:
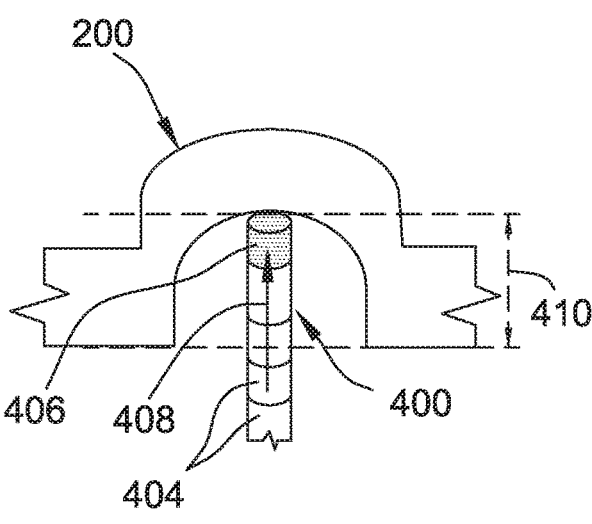
FIGS. 6-8 are additional views of the mechanical probe shown in FIG. 5, illustrating an exemplary method of using the mechanical probe to measure tissue stiffness.

An exemplary method of using the mechanical probe 400 shown in FIG. 5 to assess an ablation lesion 202 will now be described with additional reference to FIGS. 6-8. As shown in FIG. 5, the exemplary method includes initially measuring an intrinsic displacement amount of the mechanical probe 400 resulting from ventricular contraction. Specifically, prior to the ablation lesion 202 (shown in FIGS. 7 and 8) being formed at the target cardiac tissue site 200, the mechanical probe 400 is brought into contact against the target cardiac tissue site 200, while applying a minimal amount of contact force against the target cardiac tissue site 200. The displacement amount of the mechanical probe 400 resulting from ventricular contraction is measured by monitoring or recording the displacement of the position sensors 404 over a period of time, which is output to the controller 110 of the lesion assessment system 108 (shown in FIG. 1). Subsequently, as shown in FIG. 6, a pre-determined contact force 408 (e.g., 5 g) is applied to the healthy (i.e., unablated) target cardiac tissue site 200, and the resulting displacement amount 410 is measured by the plurality of sensors 404 in both the systolic and diastolic phases of the cardiac cycle. In some embodiments, a plurality of pre-determined contact forces (e.g., 5 g, 10 g, 15 g, and 20 g) is applied to the healthy target cardiac tissue site 200, and the resulting displacement for each of the plurality of pre-determined contact forces is measured by the plurality of position sensors 404. The controller 110 determines control systolic and diastolic stiffness values of the target cardiac tissue site 200 based on the mechanical response (i.e., the measured force-displacement relationship) of healthy target cardiac tissue site 200 measured by the plurality of position sensors 404.

Figure 7:
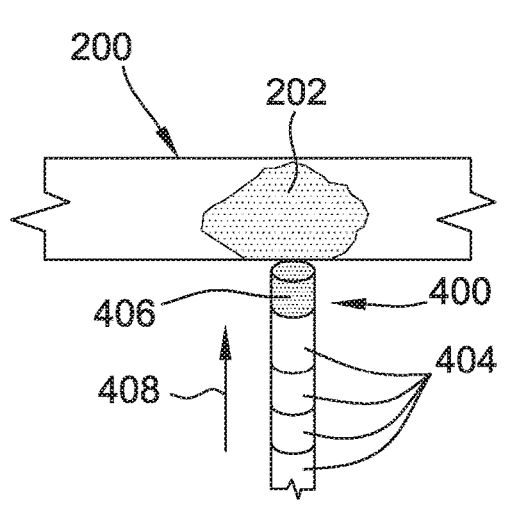
Figure 8:
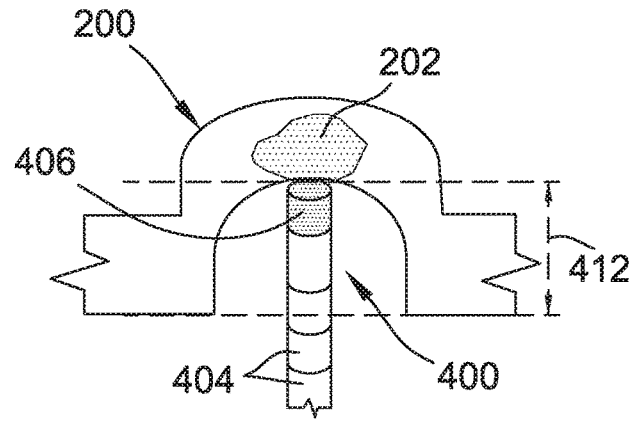

As shown in FIGS. 7 and 8, subsequent to the formation of the ablation lesion 202, the same pre-determined contact force 408 (e.g., 5 g) is applied to the ablated target cardiac tissue site 200, and the resulting displacement amount 412 is measured by the plurality of sensors 404 in both the systolic and diastolic phases of the cardiac cycle. In embodiments where a plurality of pre-determined contact forces was applied to the healthy target cardiac tissue site 200, the same plurality of pre-determined contact forces is applied to the ablated target cardiac tissue site 200, and the resulting displacement amount for each of the plurality of pre-determined contact forces is measured by the plurality of position sensors 404. The controller 110 determines systolic and diastolic stiffness values of the ablated target cardiac tissue site 200 based on the mechanical response (i.e., the measured force-displacement relationship) of the ablated target cardiac tissue site 200 measured by the plurality of position sensors 404. The transmurality value of the ablation lesion 202 is then determined by the controller 110 based on the control systolic and diastolic stiffness values, and the systolic and diastolic stiffness values of the ablated target cardiac tissue site 200 in accordance with the techniques and methods described herein.

In some embodiments, the controller 110 may be programmed to automatically record the position of the mechanical probe 400 and/or the displacement amount of the target cardiac tissue site 200 upon the pre-determined contact force being applied to the target cardiac tissue site 200 by the mechanical probe 400. Moreover, the controller 110 may be programmed to automatically record a plurality of positions and/or the displacement amounts upon a series of pre-determined contact forces being applied to the target cardiac tissue site 200 by the mechanical probe 400. In some embodiments, for example, the controller 110 is configured to automatically sequentially record the position of the mechanical probe 400 and/or the displacement amount of the target cardiac tissue site 200 for each of a plurality of pre-determined contact forces being applied to the target cardiac tissue site 200 by the mechanical probe 400.

Figure 9:
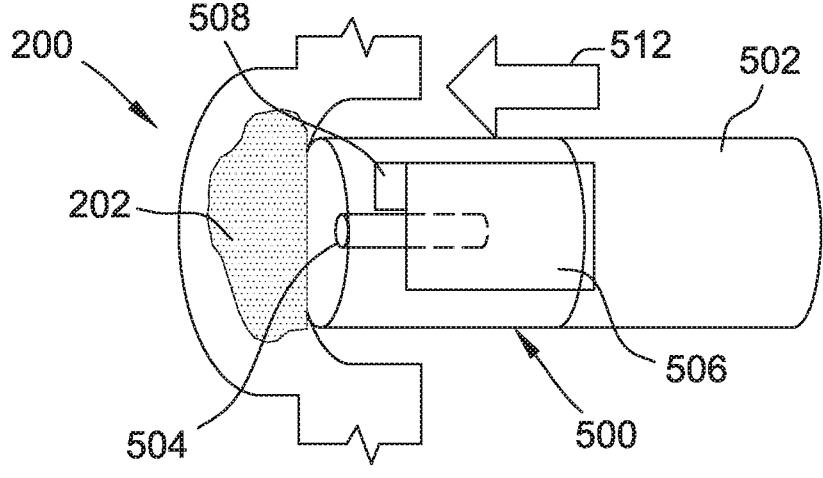
FIG. 9 is a schematic view of another exemplary embodiment of a mechanical probe suitable for use with the ablation system of FIG. 1.

FIG. 9 is a schematic view of another exemplary embodiment of a mechanical probe 500 suitable for use with the ablation system 100 of FIG. 1. In the illustrated embodiment, the mechanical probe 500 is shown adjacent to a target cardiac tissue site 200 at which an ablation lesion 202 has been formed. In this embodiment, the mechanical probe 500 is implemented as a stand-alone or dedicated catheter 502, although it should be understood that in other embodiments, the mechanical probe 500 may be implemented as part of or in combination with other catheters (e.g., ablation catheters, mapping catheters, imaging catheters, etc.). As shown in FIG. 9, the mechanical probe 500 includes a mobile pin 504 and a propulsion system 506 operatively coupled to the mobile pin 504 and configured to propel the mobile pin 504 towards the target cardiac tissue site 200. The mechanical probe 500 also includes a sensor 508 configured to measure the deceleration and/or return acceleration of the mobile pin 504 as it contacts the target cardiac tissue site 200 and springs backs. The mechanical probe 500 is communicatively coupled to the lesion assessment system 108 for outputting data and measurements (e.g., mechanical response measurements) thereto, and/or for receiving control signals therefrom.

In this embodiment, the mechanical probe 500 is configured to measure tissue stiffness based on the elasticity of cardiac tissue. More specifically, the mechanical probe 500 is configured to propel the mobile pin 504 towards the target cardiac tissue site 200 at a known speed, and measure the deceleration and/or return acceleration of the mobile pin 504 as it contacts the target cardiac tissue site 200 and springs backs. The controller 110 is configured to determine systolic and diastolic tissue stiffness values of the target cardiac tissue site 200 based on the initial speed of the mobile pin 504, the mass of the mobile pin 504, and the measured deceleration and/or return acceleration rates of the mobile pin 504.

The propulsion system 506 is operatively coupled to the mobile pin 504, and is operable to propel or drive the mobile pin 504 forward towards the target cardiac tissue site 200 when activated by an operator. The propulsion system 506 can include any suitable electrical, mechanical, and/or electromechanical devices for generating and/or transmitting kinetic energy to the mobile pin 504 to drive the mobile pin 504 towards the target cardiac tissue site 200. In some embodiments, the propulsion system 506 includes an electromotive drive, such as a solenoid coil. Additionally or alternatively, the propulsion system 506 includes a mechanical drive, such as a spring, a pneumatic drive, and/or a hydraulic drive. Other devices suitable for use in or as a propulsion system include, but are not limited to, electromagnets, permanent magnets, shape memory alloys, and piezoelectric materials.

The sensor 508 can include any suitable sensor capable of measuring the acceleration and/or deceleration of the mobile pin 504. In one exemplary embodiment, the sensor 508 includes an optical sensor configured to detect one or more optical markings on the mobile pin 504 to measure deceleration and/or reverse acceleration. In some embodiments, for example, the mobile pin 504 includes a pattern or series of optical markers spaced longitudinally along the mobile pin 504, where each optical marker is spaced at a known distance from adjacent optical markers. The optical sensor 508 detects each optical marker as the mobile pin 504 moves forward and rearward, and measures the amount of time it takes for each optical marker to pass the sensor 508. Based on the known distance between each optical marker and the amount of time it takes each optical marker to pass the sensor 508, the sensor 508 and/or the controller 110 determines the deceleration of the mobile pin 504 as it moves toward the target cardiac tissue site 200. Additionally, by measuring the same characteristics as the mobile pin 504 moves rearward, away from the target cardiac tissue site 200, the sensor 508 and/or the controller 110 can determine the return acceleration of the mobile pin 504.

An exemplary method of using the mechanical probe 500 shown in FIG. 9 to assess an ablation lesion 202 will now be described with additional reference to FIGS. 10-11. As shown in FIG. 9, the mechanical probe 500 initially makes contact with the target cardiac tissue site 200 at a predetermined contact force value 512. The pre-determined contact force value 512 may be measured, for example, using a suitable contact force sensor, such as the contact force sensor 140 shown in FIG. 2. When reaching the pre-determined contact force values in systole and diastole, the mechanical probe 500 propels the mobile pin 504 towards the target cardiac tissue site 200 using the propulsion system 506. In some embodiments, the controller 110 of the lesion assessment system 108 is configured to automatically propel the mobile pin 504 in response to the contact force sensor detecting the pre-determined amount of contact force between the mechanical probe 500 and the target cardiac tissue site 200.

Figure 10:
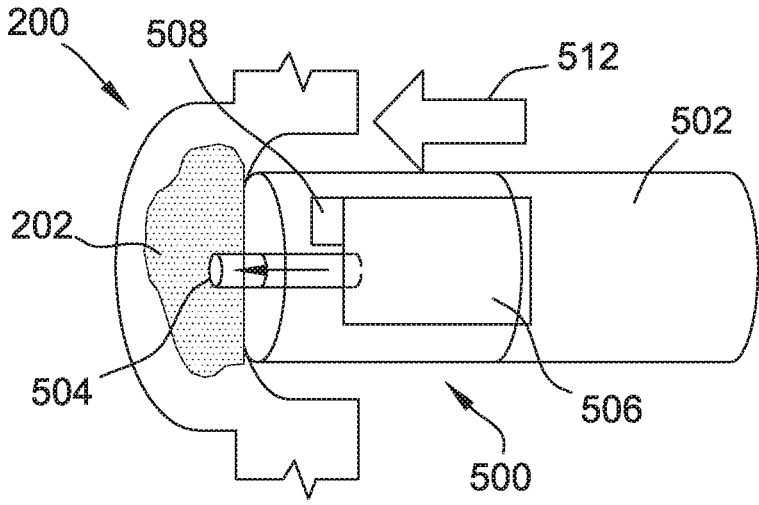
FIGS. 10-11 are additional views of the mechanical probe shown in FIG. 9, illustrating an exemplary method of using the mechanical probe to measure tissue stiffness.
Figure 11:
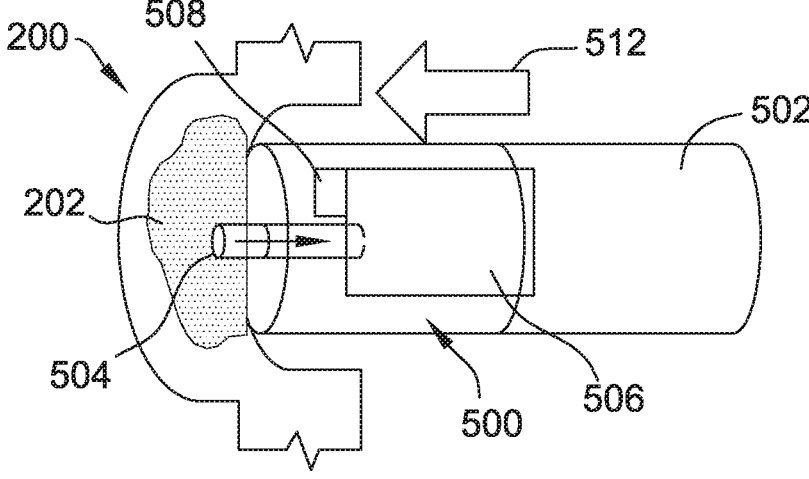

As shown in FIG. 10, as the mobile pin 504 contacts the target cardiac tissue site 200, the sensor 508 measures deceleration of the mobile pin 504. Further, as shown in FIG. 11, the elasticity of the target cardiac tissue site 200 causes the mobile pin 504 to spring back. The return acceleration of the mobile pin 504 is measured by the sensor 508. The deceleration and/or return acceleration values are recorded by the controller 110, and used in combination with the initial speed and mass of the mobile pin 504 to determine systolic and diastolic tissue stiffness values of the target cardiac tissue site 200. In some embodiments, systolic and diastolic tissue stiffness values can be based on multiple deceleration and/or return acceleration measurements recorded for different initial speeds of the mobile pin 504 in systole and diastole. The systolic and diastolic tissue stiffness values are used by the controller 110 to determine a transmurality value of the ablation lesion 202 in accordance with the techniques and methods described herein.

In some embodiments, the initial speed at which the mobile pin 504 is propelled towards the target cardiac tissue site 200 is adjusted based on the amount of contact force between the mechanical probe 500 and the target cardiac tissue site 200. In one exemplary embodiment, the initial speed of the mobile pin 504 is inversely related to the contact force applied by the mechanical probe 500 such that the force imparted to the target cardiac tissue site 200 by the mobile pin 504 does not exceed a predetermined force value (e.g., 40 g). In some embodiments, the controller 110 may be configured to automatically adjust the initial speed of the mobile pin 504 (e.g., by controlling the propulsion system 506) based on the contact force between the mechanical probe 500 and the target cardiac tissue site 200.

In some embodiments, the mechanical probe 500 may additionally or alternatively include a spring having a known spring constant positioned proximally from the mobile pin 504. The spring is axially aligned with the mobile pin 504 such that, as the mobile pin 504 springs back from the target cardiac tissue site 200, the spring is compressed by the mobile pin 504. In this embodiment, the sensor 508 may additionally or alternatively be configured to measure a compression level of the spring resulting from the return force of the mobile pin 504. The sensor 508 can include any suitable sensor capable of measuring the compression level of the spring. In some embodiments, for example, the sensor 508 includes an optical sensor configured to measure an amount of displacement of a distal end of the spring resulting from the return force of the mobile pin 504. Based on the initial speed and mass of the mobile pin 504, the compression level of the spring, and the known spring constant of the spring, the sensor 508 and/or the controller 110 determines systolic and diastolic tissue stiffness values of the target cardiac tissue site 200. These values are in turn used by the controller 110 to determine a transmurality value of the ablation lesion 202 in accordance with the techniques and methods described herein.

Figure 12:
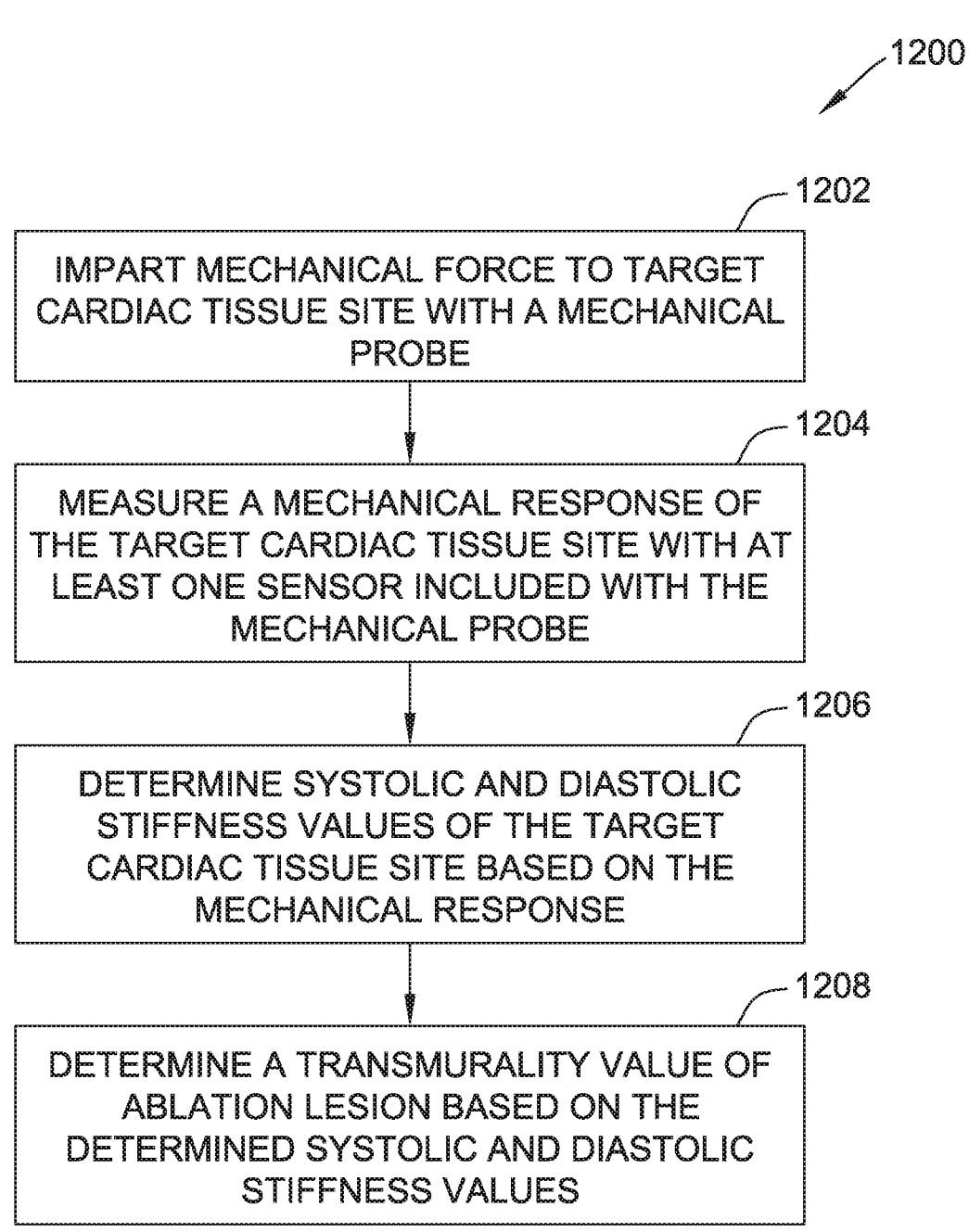
FIG. 12 is a flow diagram illustrating an exemplary method of assessing the transmurality of an ablation lesion formed at a target cardiac tissue site.

FIG. 12 is a flow diagram illustrating an exemplary method 1200 for assessing the transmurality of an ablation lesion formed at a target cardiac tissue site by an ablation catheter, such as the ablation catheter 104 shown in FIG. 1. In the illustrated embodiment, the method 1200 includes imparting 1202 mechanical force to the target cardiac tissue site with a mechanical probe (e.g., using the mechanical probe 136 shown in FIG. 2), and measuring 1204 a mechanical response of the target cardiac tissue site with at least one sensor (e.g., sensor 138) included with the mechanical probe. The method 1200 further includes determining 1206, using a controller (e.g., controller 110) communicatively coupled to the mechanical probe, systolic and diastolic stiffness values of the target cardiac tissue site based on the mechanical response. The method 1200 further includes determining 1208, using the controller, a transmurality value of the ablation lesion based on the determined systolic and diastolic stiffness values. In some embodiments, determining the transmurality value of the ablation lesion includes determining the transmurality value by determining a ratio of the systolic and diastolic stiffness values. Further, in some embodiments, the transmurality value is determined based on control systolic and diastolic stiffness values and post-ablation systolic and diastolic stiffness values. For example, the systolic and diastolic stiffness values determined at step 1206 may be post-ablation systolic and diastolic stiffness values, and the method 1200 may further include determining, using the controller, control systolic and diastolic stiffness values of the target cardiac tissue site based on a mechanical response of healthy cardiac tissue at the target cardiac tissue site measured by the mechanical probe. In such embodiments, determining 1208 the transmurality value of the ablation lesion may include determining the transmurality value based on the control systolic and diastolic stiffness values and the post-ablation systolic and diastolic stiffness values.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A lesion assessment system for assessing an ablation lesion formed at a target cardiac tissue site, the system comprising:

a mechanical probe operable to impart, through direct physical contact with the target cardiac tissue site, a mechanical force to the target cardiac tissue site, the mechanical probe comprising at least one sensor configured to measure, through the direct physical contact with the cardiac tissue site, a mechanical response of the target cardiac tissue site to the mechanical force imparted to the target cardiac tissue site; and a controller communicatively coupled to the mechanical probe and configured to:

determine systolic and diastolic stiffness values of the target cardiac tissue site based on the measured mechanical response to the mechanical force; and determine a transmurality value of the ablation lesion based on the determined systolic and diastolic stiffness values.

2. The lesion assessment system of claim 1, wherein the mechanical probe comprises a mechanical oscillator configured to impart a mechanical wave to the target cardiac tissue site through the direct physical contact with the cardiac tissue site, wherein the at least one sensor is positioned at a known distance from the mechanical oscillator and configured to detect the mechanical wave through the direct physical contact with the cardiac tissue as the mechanical wave propagates through the target cardiac tissue site, and wherein the controller is configured to determine the systolic and diastolic stiffness based on an amount of time associated with the mechanical wave traveling through the target cardiac tissue site from the mechanical oscillator to the at least one sensor.

3. The lesion assessment system of claim 2, wherein the controller is further configured to:

record a control vibration signal based on measurements taken by the at least one sensor while the mechanical oscillator is inactive;

record a vibration signal based on measurements taken by the at least one sensor while the mechanical oscillator is active; and determine an isolated vibration signal by removing the control vibration signal from the vibration signal.

4. The lesion assessment system of claim 2, wherein the mechanical probe further comprises a contact force sensor, and wherein the controller is configured to automatically output the mechanical wave in response to the contact force sensor detecting a pre-determined amount of contact force between the mechanical probe and the target cardiac tissue site.

5. The lesion assessment system of claim 1, wherein the at least one sensor comprises at least one position sensor and a contact force sensor, the at least one position sensor configured to detect a position of the mechanical probe in three-dimensional space, wherein the controller is configured to determine the systolic and diastolic stiffness values of the target cardiac tissue site based on a displacement amount of the target cardiac tissue site, measured by the at least one position sensor, resulting from a pre-determined contact force applied to the target cardiac tissue site by the mechanical probe.

6. The lesion assessment system of claim 5, wherein the controller is configured to determine the systolic and diastolic stiffness values of the target cardiac tissue site based on a plurality of displacement amounts of the target cardiac tissue site, measured by the at least one position sensor, resulting from a plurality of pre-determined contact forces applied to the target cardiac tissue site by the mechanical probe.

7. The lesion assessment system of claim 1, wherein the mechanical probe comprises a mobile pin and a propulsion system operatively coupled to the mobile pin and configured to propel the mobile pin towards the target cardiac tissue site, wherein the at least one sensor is configured to measure at least one of a deceleration rate of the mobile pin and a return acceleration rate of the mobile pin, wherein the controller is configured to determine the systolic and diastolic stiffness values based on an initial speed of the mobile pin, a mass of the mobile pin, and the at least one of the deceleration rate and the return acceleration rate.

8. The lesion assessment system of claim 1, further comprising an ablation catheter configured to ablate a target cardiac tissue site to form an ablation lesion thereon.

9. The lesion assessment system of claim 8, wherein the mechanical probe is integrated with the ablation catheter.

10. The lesion assessment system of claim 1, wherein the controller is configured to determine the transmurality value of the ablation lesion by determining a ratio of the systolic and diastolic stiffness values.

11. The lesion assessment system of claim 1, wherein the systolic and diastolic stiffness values are post-ablation systolic and diastolic stiffness values, and wherein the controller is further configured to:

determine control systolic and diastolic stiffness values based on a mechanical response of healthy cardiac tissue at the target cardiac tissue site measured by the mechanical probe; and determine the transmurality value of the ablation lesion based on the control systolic and diastolic stiffness values and the post-ablation systolic and diastolic stiffness values.

12. The lesion assessment system of claim 11, wherein the controller is configured to determine the transmurality value of the ablation lesion by determining a difference between a ratio of the control systolic and diastolic stiffness values and a ratio of the post-ablation systolic and diastolic stiffness values.

13. The lesion assessment system of claim 1, wherein the at least one sensor comprises a contact force sensor configured to measure a contact force between the mechanical probe and the target cardiac tissue site, and wherein the controller is configured to determine the systolic and diastolic stiffness values based on the mechanical response of the target cardiac tissue site measured at a pre-determined contact force between the mechanical probe and the target cardiac tissue site.

14. The lesion assessment system of claim 1, wherein the controller is further configured to:

compare the determined transmurality value to at least one of an upper threshold value and a lower threshold value; and generate, by an output device communicatively coupled to the controller, at least one of an audibly-perceptible alert and a visually-perceptible alert when the determined transmurality value is above the upper threshold value or below the lower threshold value.

* * * * *